United States Patent [19]

Soames

[11] 4,068,263

[45] Jan. 10, 1978

[54] IMAGE ANALYSIS METHODS

[75] Inventor: Michael Richard Soames, Fulbourn, England

[73] Assignee: Image Analysing Computers Limited, Royston, England

[21] Appl. No.: 627,395

[22] Filed: Oct. 30, 1975

Related U.S. Application Data

[63] Continuation of Ser. No. 144,974, May 19, 1971, abandoned, which is a continuation-in-part of Ser. No. 852,972, Aug. 18, 1969, Pat. No. 3,617,631, which is a continuation of Ser. No. 523,725, Jan. 28, 1966, abandoned.

[30] Foreign Application Priority Data

Feb. 6, 1965  United Kingdom .................. 5256/65

[51] Int. Cl.$^2$ ............................................. H04N 7/18
[52] U.S. Cl. .................................................. 358/107
[58] Field of Search ............. 358/93, 107; 235/92 MT

[56] References Cited

U.S. PATENT DOCUMENTS 2,494,441  1/1950  Hillier .................................. 235/92 R Primary Examiner—Howard W. Britton
Attorney, Agent, or Firm—Beveridge, DeGrandi, Kline & Lunsford

[57] ABSTRACT

This invention provides a method for obtaining a video signal corresponding to selected parts of an image by separating from the video signal relating to the whole image that portion relating to the selected parts. The method includes a comparison of a boundary signal derived from the separated video signal with that relating to the whole image and adjustment of the separation to correct for inaccuracies in the separated signal in respect of the boundaries of the selected parts. The invention also provides apparatus for deriving the boundary signal and displaying the two signals for visual comparison.

3 Claims, 8 Drawing Figures

MICHAEL RICHARD SOAMES

BY Beveridge & De Grandi

MICHAEL RICHARD SOAMES

By Beveridge & DeGrandi

IMAGE ANALYSIS METHODS

This is a continuation application of my U.S. patent application Ser. No. 144,974 filed May 19, 1971 now abandoned, which was a continuation-in-part application of U.S. patent application Ser. No. 852,972 filed Aug. 18, 1969, now U.S. Pat. No. 3,617,631, the latter having been a continuation of the earlier U.S. Pat. application Ser. No. 523,725 filed Jan. 28, 1966, now abandoned.

This invention and the prior applications relate to the analysis and measurement of features contained within optical images and in particular to the determination of a suitable signal discrimination level whereby the desired features may be selected from the remainder of the image.

When analysing optical images for the purpose of determining the shape and size of features contained therein, it is convenient to create a second quantised image containing only the required features and with greatly enhanced or infinite contrast and definition. However considerable difficulty is often experienced in the determination of a suitable discrimination level so as to accurately define the feature boundaries of the original image.

One possible method for determining this level involves the visual comparison of two separate images of substantially the same scale, one image containing only the features it is required to examine as described above, and the other containing both wanted and unwanted features. The discrimination level may then be adjusted until the size and shape of the features in both images appear to be the same. The image which contains only the desired features as described above may then be analysed and measurements made thereon. This method, however, involves the use of two picture reproducers such as conventional picture display monitors and the accuracy is not entirely independent of the human element.

Image analysis has many applications and may be used in making blood counts, assessing the sizes of cells in non-metallic materials, in the petrographic examination of minerals, in particle sizing and in the examination of fabrics and fibre. However the invention has a particular application in the examinatin of metallurgical specimens with a reflecting microscope and associated apparatus.

If a metallurgical specimen is polished and etched in a certain manner and viewed under a microscope, it is possible to see and examine the grain structure and non-metallic inclusion content of the specimen since the grain boundaries and non-metallic inclusions reflect light differently from the remainder of the surface of the specimen. It is therefore possible to obtain data from measurement of such specimens, regarding the grain size and non-metallic inclusion content of the particular substance under examination.

It is a first object of the present invention to provide a method for quantitativey measuring a specific part of a specimen having areas of distinctly different optical properties.

It is another object of the present invention to provide a method of setting up apparatus capable of separating video signal corresponding to a selected part of a complete image from that corresponding to the remainder of the image with provision for checking and adjusting the separation in respect of the boundary of the selected part.

It is a further object of the present invention to provide apparatus for separating video signal corresponding to a selected part of a complete image from that corresponding to the remainder of the image which includes means for demonstrating the accuracy of the separation in relation to the boundary of the selected part.

Other and further objects will be apparent from the ensuing description and upon reference to the accompanying drawings, wherein:

FIGS. 1, 2 and 3 are block schematic diagrams of embodiments of the invention incorporating simultaneous or sequential presentation by a monitor of images corresponding to the first and second video signals, FIG. 4 is a graphical representation of two video signals X and Y, the one X, corresponding to the signal output from a television camera and the other, Y, corresponding to the discriminator output signal, after selective discrimination by a discriminator in which the discrimination level is incorrectly set.

Figure 1:
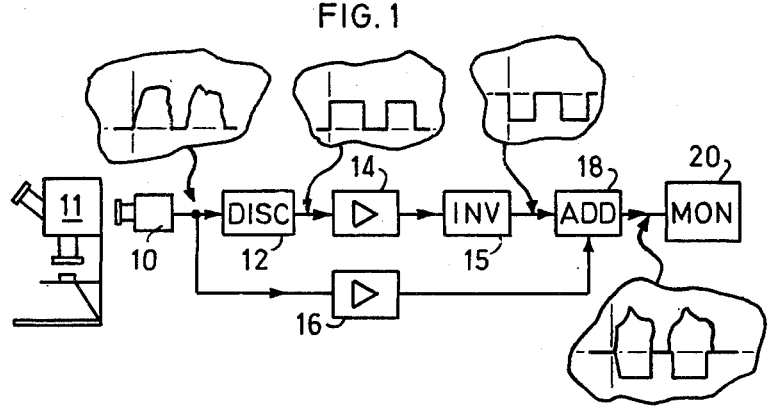

Where applicable the same reference numerals have been used throughout to indicate similar apparatus, and approximate waveforms of the signals at various junctions of each system have been included. For clarity, when comparing two superimposed waveforms a zero d.c.-level has been employed for each waveform.

Figure 7A:
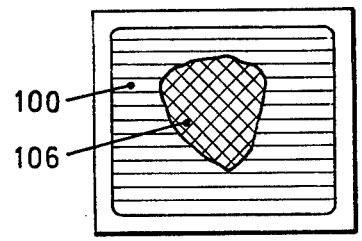
FIG. 7a represents a picture display monitor in which two images are displayed, superimposed in correct register the one on the other.
Figure 7B:
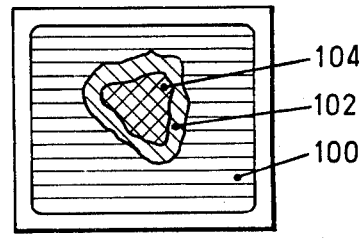
FIG. 7b represents a picture display monitor in which two images are displayed, superimposed the one on the other, in incorrect register, as the result of a wrong setting of the discrimination level.

FIG. 7b illustrates diagrammatically two images superimposed the one on the other in incorrect register, the one image 100 extending over the entire area of the screen amd containing a single feature 102, and the other comprising only the discriminated image content 104. When discrimination level is set correctly as illustrated in FIG. 7a, the boundary of this feature 104 coincides with that of the feature 102, so that the two feature images 102 and 104, appear as a single feature 106.

It may for example be desired to measure the area projection and number of the features of an image, for example the area of feature 102 in image 100, and this can be successfully performed after the discrimination level has been adjusted in the above described manner.

According to the embodiment illustrated in FIG. 1, an object to be analysed is placed under a microscope 11, and an optical system is provided whereby the optical image is transmitted to a television camera 10, and the electrical output of this camera forms a video signal which may be analysed. A discriminator 12 responsive to this video signal supplies a second signal to an amplifier 14, the output of which is supplied to a phase inverting means 15. An amplifier 16 also responsive to the first signal from the television camera supplies an amplified version of this first signal, together with the output of the inverting means 15 to the input of a mixer stage 18, wherein these two signals are combined in such a way that when applied to a conventional picture display monitor 20, two images appear, corresponding to the two signals, and superimposed the one on the other.

Figure 4:
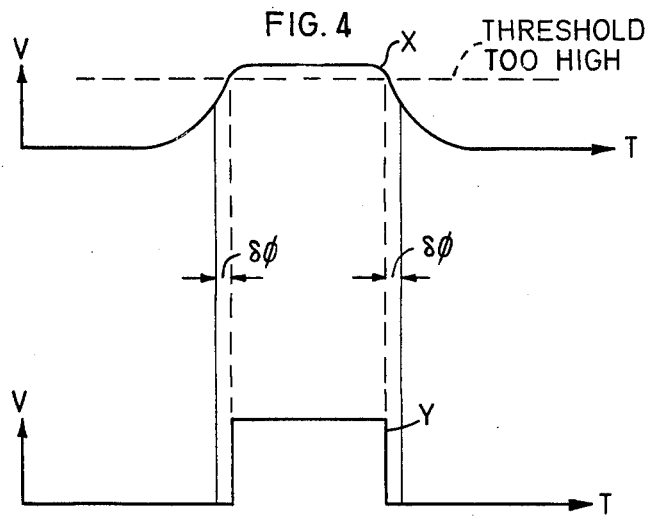

In operation, the discrimination level of the discriminator 12 is adjusted until the two images are in correct register as indicated in the simplified example illustrated in FIGS. 7a and 7b. FIG. 4 represents two video signals X and Y, the first X, corresponding to a video signal from the television camera 10, and the other Y (which is of enhanced contrast and definition) corresponding to the discriminator output signal after inversion. The signal Y, as illustrated in FIG. 4 is of insufficient width due to incorrect setting of the discriminator threshold (discrimination level) such as illustrated in FIG. 7b, and the difference between the two signals, X, Y indicated by $S\phi$, can be reduced to a minimum, by adjusting the discrimination level of the discriminator, 12.

Figure 2:
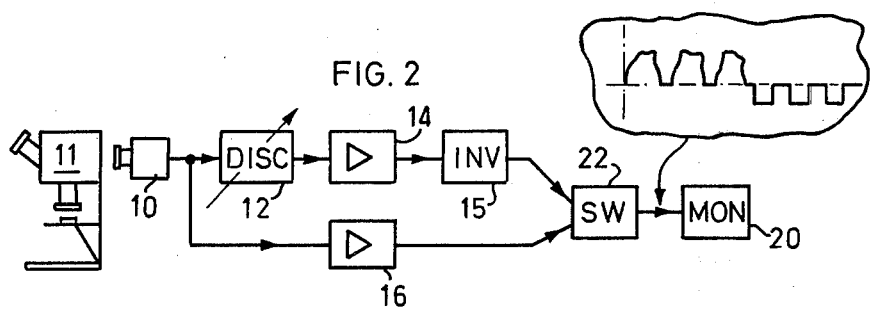

In the embodiment as illustrated in FIG. 2 the mixer stage 18 is replaced by a switching stage 22 whereby the two signals are sequentially applied to the monitor 20, so that the images appear the one after the other in succession, and the two images may be registered as before described by adjustment of the discrimination level of the discriminator 12.

Alternatively the switching stage 22 may be adapted to switch the signals so that the image produced by the display monitor 20 comprises a plurality of parallel bands which alternately contain the image content of one or the other of the two video signals, and the two signals may be correctly registered as before described by adjustment of the discrimination level of the discriminator 12.

Figure 3:
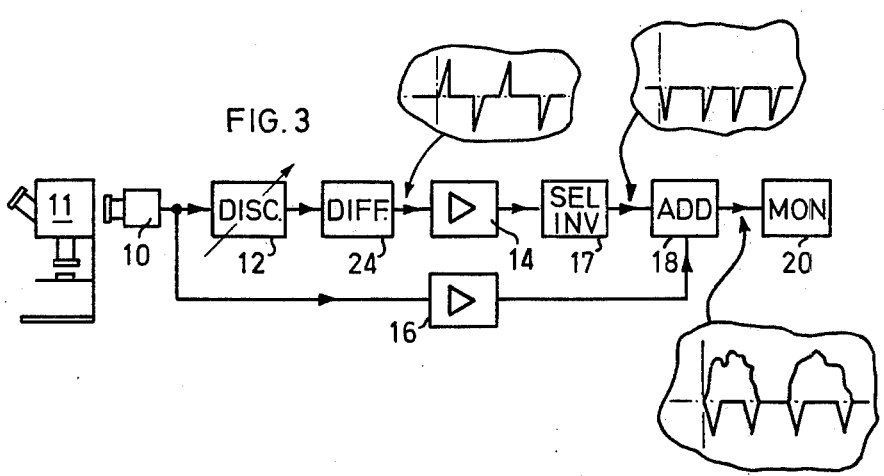

In the embodiment illustrated in FIG. 3 the video signal from the discriminator 12 is differentiated by a differentiating stage 24. The resulting signal comprises a series of pulses which correspond to the slope of the leading and trailing edges of the pulses derived from the discriminator 12. After amplification by an amplifier 14, the differentiated signals are selectively inverted by an inverting stage 17 to form a boundary signal in which the pulses are uni-directional. It will be seen that the amplitude change of the differentiated and selectively inverted pulses forming the boundary signal, is opposite to the amplitude change in the video signal caused by the feature relative to the surrounding background, so that when displayed on a television monitor the boundary signal will be readily distinguishable from the feature and the background. This uni-directional pulse train is then combined in the adding circuit 18 with an amplified version of the original video signal before discrimination in the same manner as hereinbefore described.

Although an inverter stage has been included in the illustrated embodiments it is not essential to include this stage, and it may be omitted, in which case the two images displayed on the monitor will appear in similar phase.

The embodiments illustrated in FIGS. 1 to 3 refer to systems wherein the discrimination level is adjustable in response to a visual indication of the original and discriminated signals.

It will be readily apparent to anyone skilled in the art that many alternative circuit arrangements may be used to perform the discrimination and differentiation of the video signals. However two possible circuits are illustrated in FIGS. 5 and 6 but these are only intended to illustrate two possible arrangements.

Figure 5:
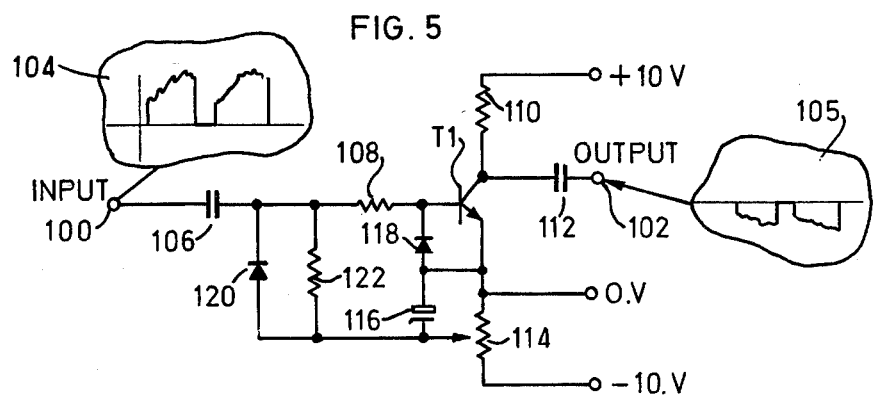
FIG. 5 illustrates one possible arrangement of a discriminator circuit.
Figure 6:
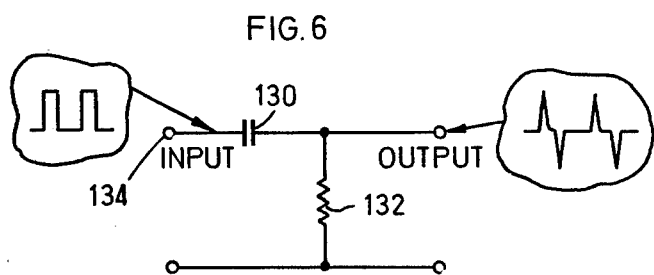
FIG. 6 illustrates one possible arrangement of a differentiating circuit.

FIG. 5 illustrates a discriminator circuit for supplying at its output terminal 102 an amplitude discriminated version of an input signal 104 which is applied to its input terminal 100. The input signal 104 is applied to the base of a transistor T1 through a capacitor 106 and a resistor 108, connected in series, while the discriminated output signal 105 appears across the collector lead resistor 110, which is connected between the collector of the transistor T1 and a source of positive potential of +10 volts. The output signal 105 is applied to the output terminal 102 through a capacitor 112.

The emitter of the transistor T1 is connected directly to a point of zero potential (relative to said source of positive potential) and a potentiometer 114 is connected between the emitter and a source of negative potential of −10 volts (relative to the point of zero potential). A capacitor 116 which is preferably an electrolytic capacitor of relatively large capacitance is connected between the variable tapping of the potentiometer 114 and the emitter of the transistor T1 and a diode 118 is connected between the emitter and base of the transistor. A second diode 120 is connected between the junction between the capacitor 106 and the resistor 108 and the variable tapping of the potentiometer 114 a resistor 122 being connected in parallel with this second diode 120.

By varying the position of the tapping of the potentiometer 114 the base current of the transistor T1 may be varied and the base bias correspondingly varied. If the reference level potential of the video input signal is zero volts and the base is maintained substantially at a potention of zero volts, the transistor T1 will conduct during the whole of each video signal pulse, whereas if the base is maintained at a negative potential of −V volts, and the reference level potential of the input signal remains the same, the transistor T1 will only conduct for the time interval when the amplitude of each positive going video signal pulse exceeds +V volts. In this way the discrimination level of the discriminator may be varied by varying the position of the tapping of the potentiometer 114.

FIG. 6 illustrates a differentiating circuit which comprises a capacitor 130 and a resistor 132. By arranging that the reactance of the capacitor 130 is very much greater than the resistance of the resistor 132 at the frequency of the video input signal applied to the input terminal 134, the voltage which appears across the resistor 132 will comprise a series of voltage pulses corresponding to the leading and trailing edges of the video signal pulses, the amplitude of each voltage pulse being substantially proportional to the slope of the corresponding leading or trailing pulse edge. Consequently the waveform of the signal appearing across the resistor 132 can be said to correspond substantially to the first differential of the waveform of the video signal applied to the input terminal 134.

I claim:

1. A method of quantitatively measuring a specific part of a specimen having areas of distinctly different light-reflective optical properties comprising the steps of scanning an image of the specimen and producing an electrical video signal corresponding to the complete image and containing signal content both of the specific part and the remainder of the image, modifying the video signal with a discriminator which is adjustable to remove signal content of the remainder of the image and provide an output signal of enhanced contrast and definition corresponding to the specific part of the complete picture, differentiating the output signal to provide an edge signal corresponding to the boundary of the specific part, providing a visual display on a picture display monitor of the video signal and the edge signal, comparing the display corresponding to the video signal and the edge signal, adjusting the discrimination level of said discriminator in direct response to the result of the comparison of the two signals to minimize any differences between the boundaries of the specific parts arising from the two signals, and making measurements on the discriminator output signal corresponding to the specific part of the complete picture.

2. A method of quantitatively measuring a specific part of a specimen having areas of distinctly different light-reflective or transmittive properties comprising the steps of scanning an image of the specimen and producing an electrical video signal corresponding to the complete image and containing signal content both of the specific part and the remainder of the image, modifying the video signal with the discriminator which is adjustable to remove signal content of the remainder of the image and provide an output signal of enhanced contrast and definition corresponding to the specific part of the complete picture, inverting the phase of the discriminator output signal, providing a visual display on a picture display monitor of the video signal and the inverted discriminator output signal, comparing the displays corresponding to the video signal and the inverted discriminator output signal, adjusting the discrimination level of said discriminator in direct response to the result of the comparison of the two signals to minimize any differences between the boundaries of the specific parts arising from the two signals, and making measurements on the discriminator output signal corresponding to the specific part of the complete picture.

3. A method of quantitatively measuring a specific part of a specimen having areas of distinctly different light-reflective or transmittive properties comprising the steps of:

scanning an image of the specimen and producing an electrical video signal corresponding to the complete image and containing signal content both of the specific part and the remainder of the image, modifying the video signal with a discriminator which is adjustable to remove signal content of the remainder of the image and to provide an output signal of enhanced contrast and definition corresponding to the specific part of the complete picture, differentiating the discriminator output signal, selectively phase inverting the differentiated signal pulses so as to obtain unidirectional pulses, supplying the video signal and the unidirectional pulses to a picture display monitor to provide a visual display of the video signal and unidirectional pulses, comparing the two displays corresponding to the video signal and the unidirectional pulses, adjusting the discrimination level of the discriminator in direct response to the result of the comparison of the two signals to minimize any difference between the boundaries of the specific parts arising from the two signals, and making measurements on the discriminator output signal pulses corresponding to the specific part of the complete picture.

* * * * *